(12) United States Patent
Nirogi et al.

(10) Patent No.: US 12,285,421 B2
(45) Date of Patent: Apr. 29, 2025

(54) USES OF A 5-HT4 RECEPTOR AGONIST (71) Applicant: SUVEN LIFE SCIENCES LIMITED, Hyderabad-Telangana (IN)

(72) Inventors: Ramakrishna Nirogi, Hyderabad (IN); Abdul Rasheed Mohammed, Hyderabad (IN); Anil Karbhari Shinde, Hyderabad (IN); Venkata Ramalingayya Grandhi, Hyderabad (IN); Pradeep Jayarajan, Hyderabad (IN); Vijay Benade, Hyderabad (IN); Gopinadh Bhyrapuneni, Hyderabad (IN); Venkateswarlu Jasti, Hyderabad (IN)

(73) Assignee: SUVEN LIFE SCIENCES LIMITED, Hyderabad-Telangana (IN)

( * ) Notice: Subject to any disclaimer, the term of this patent is extended or adjusted under 35 U.S.C. 154(b) by 746 days.

(21) Appl. No.: 17/285,815

(22) PCT Filed: Oct. 17, 2019

(86) PCT No.: PCT/IB2019/058853
§ 371 (c)(1),
(2) Date: Apr. 15, 2021

(87) PCT Pub. No.: WO2020/079630
PCT Pub. Date: Apr. 23, 2020

(65) Prior Publication Data
US 2021/0386727 A1 Dec. 16, 2021

(30) Foreign Application Priority Data
Oct. 18, 2018 (IN) .............................. 201841039516

(51) Int. Cl.
*A61K 31/454* (2006.01)
*A61P 25/24* (2006.01)
*A61P 25/28* (2006.01)

(52) U.S. Cl.
CPC ............ *A61K 31/454* (2013.01); *A61P 25/24* (2018.01); *A61P 25/28* (2018.01)

(58) Field of Classification Search
CPC ......... A61K 31/454; A61P 25/24; A61P 25/28
See application file for complete search history.

(56) References Cited

U.S. PATENT DOCUMENTS

| 9,636,335 B2 | 5/2017 | Nirogi et al. |
| 2017/0283359 A1 | 10/2017 | Nirogi et al. |

FOREIGN PATENT DOCUMENTS

| WO | WO-2016027277 A1 * | 2/2016 | ............... A61P 25/16 |

OTHER PUBLICATIONS

Sepehry, A. A., Lee, P. E., Hsiung, G. Y. R., Beattie, B. L., & Jacova, C. Effect of Selective Serotonin Reuptake Inhibitors in Alzheimer's Disease with Comorbid Depression. Drugs & Aging, 29(10), 793-806. https://doi.org/10.1007/s40266-012-0012-5 (Year: 2012).*
Becker, M., Pinhasov, A., & Ornoy, A. Animal Models of Depression: What Can They Teach Us about the Human Disease? Diagnostics, 11(1), 123. https://doi.org/10.3390/diagnostics11010123 (Year: 2021).*
European Patent Office, International Search Report, PCT/IB2019/058853, Jan. 15, 2020, Rijswijk, Netherlands.
European Patent Office, Written Opinion, PCT/IB2019/058853, Jan. 15, 2020, Rijswijk, Netherlands.
Muddana Nageswararao et al, "Suvn-d4010: A novel 5-ht4receptor partial agonist for the treatment of Alzheimer's disease", Alzheimer's & Dementia: The Journal of the Alzheimer'sAssociation,vol. 11, No. 7, Jul. 2015 (Jul. 2015), XP029353774. DOI: 10.1016/J.JALZ.2015.06.524 ISSN:1552-5260 (D2).
Bachurin Sergey O et al, "Mild cognitive impairment due to Alzheimer disease: Contemporary approaches to diagnostics and pharmacological intervention", Pharmacological Research, Academic Press, London, GB,vol. 129, Nov. 21, 2017 (Nov. 21, 2017), p. 216-226, XP085353400. DOI: 10.1016/J.PHRS.2017.11.021 ISSN:1043-6618 (D3).
Jol Bockaert et al, "5-HTreceptors, a place in the sun: act two", 2011, vol. 11, No. 1, p. 87-93, XP028186429. DOI: 10.1016/J.COPH.2011.01.012 ISSN: 1471-4892 (D4).
Bhyrapuneni Gopinadh et al, "SUVN-D4010: A Potent and Selective 5-HT4Receptor Partial Agonist—Assessment of Safety, Tolerability and Pharmacokinetics in Healthy Human Volunteers", Alzheimer's & Dementia: The Journal of the Alzheimer'sAssociation,vol. 13, No. 7, Jul. 2017 (Jul. 2017), XP085216260. DOI: 10.1016/J.JALZ.2017.06.476 ISSN:1552-5260.
JAMA, 2004, 291, 47-53.
JAMA, 2002, 288, 321-333.
Neuroscience Letters 2016, 616, 197-203.
Exp. Gerontol. 2003, 38, 159-66.
Curr. Drug Targets, 2004, 3, 39-51.
Neuropsychiatr Dis Treat. 2006, 2(4), 531-536.

(Continued)

Primary Examiner — Yih-Horng Shiao
Assistant Examiner — Hoi Yan Lee
(74) Attorney, Agent, or Firm — IPHORGAN LTD (57) ABSTRACT

The present invention relates to new uses of a 5-HT$_4$ receptor agonist, specifically Isopropyl-3-{5-[1-(3-methoxypropyl)piperidin-4-yl]-[1,3,4]oxadiazol-2-yl}-1H-indazole (Compound-1) or a pharmaceutically acceptable salts thereof, for the treatment of dementia due to menopause, senile dementia, cognitive deficits associated with schizophrenia, depression, chemotherapy-induced cognitive impairment, and behavioral and psychological symptoms of dementia such as apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders. The present invention further provides use of the 5-HT4 receptor agonist in the manufacture of medicament intended for the treatment of the disorders described herein.

4 Claims, 5 Drawing Sheets

(56) References Cited

OTHER PUBLICATIONS

Clin Psychopharmacol Neurosci, 2018, 16 (1), 7-17.
Clin Cancer Res, 2012, 18(7), 1954-1965.
Psychiatry Investig, 2017, 14 (3), 271-280.
Yohn, Christine N., Mark M. Gergues, and Benjamin Adam Samuels. "The role of 5-HT receptors in depression." Molecular Brain 10:28, pp. 1-12 (2017).
Myers, Jamie S. "Chemotherapy-Related Cognitive Impairment." Clinical Journal of Oncology Nursing vol. 13(4) (2009): 413-21.
Roth, Bryan L., S. Mohammad Hanizavareh, and Andrew E. Blum. "Serotonin receptors represent highly favorable molecular targets for cognitive enhancement in schizophrenia and other disorders." Psychopharmacology 174 (2004): 17-24.
Gray, John A., and Bryan L. Roth. "Molecular targets for treating cognitive dysfunction in schizophrenia." Schizophrenia Bulletin 33, No. 5 (2007): 1100-1119.
Lucas, Guillaume, Vladimir V. Rymar, Jenny Du, Ouissame Mnie-Filali, Christina Bisgaard, Stella Manta, Laura Lambas-Senas et al. "Serotonin4 (5-HT4) receptor agonists are putative antidepressants with a rapid onset of action." Neuron 55, No. 5 (2007): 712-725.
Rabasseda, X., and V. L. Mason. "Suven's Therapeutics for the Potential Treatment of Cognitive Deficits Associated With Degenerative Diseases" 43rd Annual Meeting of the Society for Neuroscience (SFN), San Diego, California, USA—Nov. 9-13, 2013. Drugs of the Future 38, No. 12, p. 853 (2013). (Abstract).
Ahmad, Ishtiyaque, and Ramakrishna Nirogi. "5-HT4 Receptor agonists for the treatment of alzheimer's disease." Neurosci. Med 2 (2011): 87-92.
Cho, Seongeun, and Yun Hu. "Activation of 5-HT4 receptors inhibits secretion of β-amyloid peptides and increases neuronal survival." Experimental Neurology 203, No. 1 (2007): 274-278.
Bogdanova et al., "Factors influencing behavior in the forced swim test" Physiology and Behavior, vol. 118:227-239 (2013).

\* cited by examiner

Figure 1

Data represents Mean ± SEM of discriminative index. ****$p$<0.0001 vs. vehicle group (One-way ANOVA followed by Bonferroni's posthoc test) n= 12.

Figure 2

Data represents Mean ± SEM of discriminative index. *$p$<0.05 vs. vehicle (One-way ANOVA followed by Bonferroni's posthoc test), n=6-9.

Figure 3

Data represents Mean ± SEM of discriminative index. *$p<0.05$, **$p<0.01$ vs. MK-801 (One-way ANOVA followed by Dunnett's multiple comparison test) n=7-11.

Figure 4

Vehicle, 4 mL/kg, *p.o.*

Compound-1, 3 mg/kg, *p.o.*

Data represents Mean ± SEM of Dominance levels (Repeated measures ANOVA followed by Tukey's multiple comparison test), *$p<0.05$, vs $2^{nd}$ week, n=10.

Figure 5

Percent change from mean basal value.

Area under the curve (AUC) values for change in serotonin.

Data expressed as Mean ± SEM. ***$p<0.001$ Vs Compound-1, #$p<0.05$ Vs paroxetine.

Figure 6

Data represents Mean ± SEM of duration of attack, Student's paired t-test, **p<0.01 vs basal, n=12.

Figure 7

Data represents Mean ± SEM of duration of immobility (s), *p<0.05, ****p<0.0001 vs. vehicle one-way ANOVA followed by Dunnett's multiple comparisons test, n=10.

USES OF A 5-HT4 RECEPTOR AGONIST

CROSS REFERENCE TO RELATED APPLICATIONS

This application is a national stage completion application of PCT Application No. PCT/IB2019/058853, filed Oct. 17, 2019, and claims priority from India Application No. 201841039516, filed Oct. 18, 2018. Each of these applications is incorporated by reference herein in its entirety.

FIELD OF THE INVENTION

The present invention relates to the new uses of a 5-HT$_4$ receptor agonist, specifically Isopropyl-3-{5-[1-(3-methoxypropyl) piperidin-4-yl]-[1,3,4]oxadiazol-2-yl}-1H-indazole or a pharmaceutically acceptable salt thereof, for the treatment of dementia due to menopause, senile dementia, cognitive deficits associated with schizophrenia, depression, chemotherapy-induced cognitive impairment, and behavioral and psychological symptoms of dementia such as apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders. The present invention further provides use of the said compounds in the manufacture of medicament intended for the treatment of the disorders described herein.

BACKGROUND OF THE INVENTION

Cognitive decline occurs in women during menopause. Roughly two-thirds of women complain of forgetfulness during menopause. Empirical evidences suggest peri- and post-menopausal women performed worse on tests of memory and cognition in the year after they had their last period than in the time leading up to menopause. In peri- and post-menopausal women reached this state either naturally or by oophorectomy, cognitive function significantly declines due to chronic state of hormonal deprivation. Dementia in post-menopausal women affects various components, viz., verbal, episodic, visuo-spatial navigation along with deficits of attention and executive function which affects activities of daily living and thereby quality of life (QOL) negatively. The decline in memory is usually most pronounced within 12 months after the final menstrual period. In most of the women, cognitive function is not likely to worsen in post-menopause in any pattern other than that expected with normal aging. Although it is not likely that in post-menopause, a woman's cognitive function will return to what it was in pre-menopause, the women may adapt to and compensate for the symptoms with time.

Hormone replacement therapy (HRT) was once considered to be the first line treatment strategy in post-menopause women for the abnormal physiological changes and disabilities that are unavoidable. However, the recent studies conducted in menopausal women (WHIMS-Women's Health Initiative Memory Study) concluded the negative effects of HRT along with an increased risk of uterine, ovarian and breast cancers, pulmonary embolism, cardiac disease and stroke (*JAMA,* 2004, 291, 47-53, *JAMA,* 2002, 288, 321-333). No alternative and effective therapy is approved till date in this population although some of the cholinesterase inhibitors have been tested clinically. In general, women spend one third of their life time in a state of chronic hormonal deprivation, i.e. menopause, considering an age of 50 years where they undergo menopause transition.

The 5-HT$_4$ receptors are highly expressed in brain regions like hippocampus, amygdala and cerebral cortex suggesting the involvement of receptor in cognitive processes (*Curr. Opin. Pharmacol.* 2011, 11, 87-93). 5-HT$_4$ receptors may play an important role in cognition processes through an interaction between the cholinergic and/or histaminergic systems in the hippocampus or in the cortical areas. Stimulation of 5-HT$_4$ receptors increases extracellular histamine and acetylcholine levels in rodents in these brain regions involved in cognitive function (Neuroscience Letters 2016, 616, 197-203). The 5-HT$_4$ receptor agonists modulate amyloid precursor protein (APP) derived peptides, amyloid beta (Aβ) and soluble amyloid precursor protein alpha (sAPPα) (*Exp. Gerontol.* 2003, 38, 159-66). The sAPPα is non-amyloidogenic protein and it is reported to have potent neuroprotective role against neurotoxic effects of glutamate and β-amyloid. 5-HT$_4$ receptor agonist also increases the neurotransmitter acetylcholine levels which are involved in cognitive processes (*Curr. Drug Targets,* 2004, 3, 39-51).

Unexpectedly it has been found that the 5-HT$_4$ receptor agonist of the present invention reversed the memory deficits in an animal model of menopause. Thus, 5-HT$_4$ receptor agonist of the present invention could be a potential drug candidate for the treatment of menopause related memory and cognitive loss.

Senile dementia is a disease caused by degeneration of the brain cells and is characterized by a decrease in cognitive abilities. This may include the person's ability to concentrate, to recall information, and to properly judge a situation. Senility is a deterioration of body and mind associated with advanced aging. Indications of old age vary in the time of their appearance. Surprisingly, 5-HT$_4$ receptor agonist of the present invention improved the memory in an animal model of senility.

Apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders are the common behavioral and psychological symptoms in dementia patients. These behavioral and psychological symptoms cause great agony to dementia patients and caregivers. Therefore, there remains an unmet medical need for the treatment of the behavioral and psychological symptoms of dementia. The 5-HT$_4$ receptor agonist of the present invention unexpectedly decreases the aggression levels and hence could be the potential treatment for behavioral and psychological symptoms of dementia such as apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders.

Cognitive dysfunction is a core feature of schizophrenia. Deficits are moderate to severe across several domains, including attention, working memory, verbal learning and memory, and executive functions (*Neuropsychiatr Dis Treat.* 2006, 2(4), 531-536; *Clin Psychopharmacol Neurosci,* 2018, 16 (1), 7-17). No treatment is approved for the treatment of cognitive deficits associated with schizophrenia. Surprisingly, the 5-HT$_4$ receptor agonist of the present invention improved the memory in an animal model of cognitive deficits in schizophrenia.

Cancer is a group of diseases characterized by uncontrolled growth and dissemination of abnormal cells, which is second leading cause of death globally following cardiovascular diseases. With the improved cancer survival rates globally with the advanced therapeutic strategies, research focus has been turned towards "cancer survivorship" for improving the QOL in global cancer survivors. For many patients afflicted with malignancies or cancer, chemotherapy offers the best option for disease control. Even before opting surgical and radiation procedures in cancer therapy, chemotherapy is an invaluable tool to lessen the burden of cancer and moreover, it is advised for a more fruitful outcome among above procedures. Though chemotherapy is an effective way to treat many types of cancer, it also carries negative side effects. Due to non-specific nature of cell killing by chemotherapy, neuronal cells are not an exception that underlies the neurobiology of "chemobrain" and the associated cognitive deficits. Patients treated with chemotherapy are at an increased risk of altered brain structure and function. Clinical studies indicated that up to 70% of cancer patients who received chemotherapy experience cognitive impairment (Clin Cancer Res, 2012, 18(7), 1954-1965). This cognitive impairment, commonly named "chemobrain," can affect working memory, attention, processing speed, concentration and executive functions. Deficits observed with "chemobrain" are long lasting, even up to 10 years from the last chemo received. So far, no therapeutic intervention is available or approved for global cancer survivor population. Unexpectedly, the $5\text{-}HT_4$ receptor agonist of the present invention improved the memory in an animal model of memory deficits associated with chemotherapy.

Alzheimer's disease (AD) and depression are common mental health problems among the elderly. AD is generally accompanied by various neuropsychiatric symptoms (NPSs). It is especially known to be accompanied by depressive symptoms in its early stage (*Psychiatry Investig*, 2017, 14 (3), 271-280) but the association between the severity of AD and the prevalence of depression is not yet clear. Depression in AD is very common and its prevalence in AD population is about 50%, but the rate may vary depending on the diagnostic method, degree of depression, and study population. Additionally, according to a long-term prospective study, the occurrence of depression during the progress of dementia or mild cognitive impairment seems more common than in the general population. The $5\text{-}HT_4$ receptor agonist of the present invention showed antidepressant activity in an animal model of depression. In addition to showing the standalone efficacy, the $5\text{-}HT_4$ receptor agonist of present invention, in combination with a selective serotonin reuptake inhibitor (SSRI) produced synergistic effect on extracellular levels of serotonin (5-HT) in ventral hippocampus suggesting that combined administration of a selective serotonin reuptake inhibitor and a $5\text{-}HT_4$ receptor agonist of present invention enhances 5-HT neurotransmission and offers a potential in the treatment of depression.

Currently, no drug is approved for the treatment of dementia due to menopause, senile dementia, cognitive deficits associated with schizophrenia, chemotherapy-induced cognitive impairment, and behavioral and psychological symptoms of dementia such as apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders. These cognitive, and behavioral and psychological symptoms cause great agony to patients suffering from cognitive impairment and to their caregivers. Therefore, there remains an unmet medical need for the treatment of dementia due to menopause, senile dementia, cognitive deficits associated with schizophrenia, chemotherapy-induced cognitive impairment, and behavioral and psychological symptoms of dementia such as apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders. Unexpectedly, the $5\text{-}HT_4$ receptor agonist of the present invention significantly reversed the memory deficits in various animal models indicating that it could be a potential drug candidate for the treatment of menopause related memory and cognitive loss, senile dementia, cognitive deficits associated with schizophrenia, chemotherapy-induced cognitive impairment, and behavioral and psychological symptoms of dementia.

SUMMARY OF THE INVENTION

The objective of the present invention is to provide method for treating diseases or disorders mediated through $5\text{-}HT_4$ receptor using a $5\text{-}HT_4$ receptor agonist; wherein the $5\text{-}HT_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In first aspect, the present invention relates to a method of treating dementia due to menopause, senile dementia, cognitive deficits associated with schizophrenia, depression, chemotherapy-induced cognitive impairment and, behavioral and psychological symptoms of dementia comprising administering to a patient in need thereof, a therapeutically effective amount of a $5\text{-}HT_4$ receptor agonist, wherein the $5\text{-}HT_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another aspect, the present invention relates to a method of treating dementia due to menopause comprising administering to a patient in need thereof, a therapeutically effective amount of a $5\text{-}HT_4$ receptor agonist, wherein the $5\text{-}HT_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another aspect, the present invention relates to a method of treating senile dementia comprising administering to a patient in need thereof, a therapeutically effective amount of a $5\text{-}HT_4$ receptor agonist, wherein the $5\text{-}HT_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another aspect, the present invention relates to a method of treating cognitive deficits associated with schizophrenia comprising administering to a patient in need thereof, a therapeutically effective amount of a $5\text{-}HT_4$ receptor agonist, wherein the $5\text{-}HT_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another aspect, the present invention relates to a method of treating depression comprising administering to a patient in need thereof, a therapeutically effective amount of a $5\text{-}HT_4$ receptor agonist, wherein the $5\text{-}HT_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another aspect, the present invention relates to method of treating depression comprising administering to a patient in need thereof, a therapeutically effective amount of $5\text{-}HT_4$ receptor agonist and a selective serotonin reuptake inhibitor; wherein the $5\text{-}HT_4$ receptor agonist is Isopropyl-3-{5-[1-(3- methoxypropyl) piperidin-4-yl]-[1,3,4]oxadiazol-2-yl}-1H-indazole or a pharmaceutically acceptable salt thereof.

In another aspect, the present invention relates to a method of treating chemotherapy-induced cognitive impairment comprising administering to a patient in need thereof, a therapeutically effective amount of a 5-$HT_4$ receptor agonist, wherein the 5-$HT_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another aspect, the present invention relates to a method of treating behavioral and psychological symptoms of dementia comprising administering to a patient in need thereof, a therapeutically effective amount of a 5-$HT_4$ receptor agonist, wherein the 5-$HT_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another aspect, the present invention relates to use of the 5-$HT_4$ receptor agonist, specifically Isopropyl-3-{5-[1-(3-methoxypropyl) piperidin-4-yl]-[1,3,4]oxadiazol-2-yl}-1H-indazole or a pharmaceutically acceptable salt thereof, for the treatment of dementia due to menopause, senile dementia, cognitive deficits associated with schizophrenia, depression, chemotherapy-induced cognitive impairment, and behavioral and psychological symptoms of dementia such as apathy/indifference, agitation, aggression, depression, anxiety, irritability/lability, dysphoria, aberrant motor behavior, delusions, hallucinations, elation/euphoria, psychosis, disinhibition sleep and night time behavior disorders or appetite and eating disorders.

In another aspect, the present invention relates to use of a 5-$HT_4$ receptor agonist specifically Isopropyl-3-{5-[1-(3-methoxypropyl) piperidin-4-yl]-[1,3,4]oxadiazol-2-yl}-1H-indazole or a pharmaceutically acceptable salt thereof, in combination with a selective serotonin reuptake inhibitor for the treatment of depression.

In another aspect, the present invention relates to a pharmaceutical composition for use in treating dementia due to menopause, senile dementia, cognitive deficits associated with schizophrenia, depression, chemotherapy-induced cognitive impairment, and behavioral and psychological symptoms of dementia comprising a 5-$HT_4$ receptor agonist, Isopropyl-3-{5-[1-(3-methoxypropyl) piperidin-4-yl]-[1,3,4]oxadiazol-2-yl}-1H-indazole or a pharmaceutically acceptable salt thereof and pharmaceutically acceptable excipients thereof.

DETAILED DESCRIPTION OF THE INVENTION

Unless otherwise stated, the following terms used in the specification and claims have the meanings given below:

The term, "5-$HT_4$ receptor agonist" as used herein refers to a ligand or drug that has affinity towards serotonin 5-$HT_4$ receptor, enhances or improves the function of the 5-$HT_4$ receptor. Example of the 5-$HT_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

Examples of pharmaceutically acceptable salt of the above identified compound include but not limited to, Isopropyl-3-{5-[1-(3-methoxypropyl) piperidin-4-yl]-[1,3,4] oxadiazol-2-yl}-1H-indazole oxalate.

The term, "selective serotonin reuptake inhibitor" as used herein is a chemical or drug that selectively inhibits the reabsorption or reuptake of serotonin in the brain, making more serotonin available. Examples of selective serotonin reuptake inhibitor are paroxetine, citalopram, escitalopram, fluoxetine, sertraline, dapoxetine and vilazodone or a pharmaceutical salt thereof. More preferably the selective serotonin reuptake inhibitor is paroxetine or a pharmaceutical salt thereof.

The term, "dementia due to menopause" as used herein refers to cognitive decline, memory loss, forgetfulness or memory impairment in a peri-menopausal or post-menopausal or ovariectomized female population.

The term, "senile dementia" as used herein refers to dementia due to natural aging that occurs in aged population.

The term, "cognitive deficits associated with in schizophrenia" as used herein refers to cognitive deficits of schizophrenia (one of the core symptoms) that evolve during the course of schizophrenia. The deficits are moderate to severe across several domains, including attention, working memory, verbal learning and memory, and executive functions.

The term, "depression" as used herein refers to a mental health disorder characterised by persistently depressed mood or loss of interest in activities, causing significant impairment in daily life.

The term, "chemotherapy-induced cognitive impairment" as used herein refers to chemobrain, means cognitive changes that occur as a side effect of chemotherapy. These changes may be temporary changes in memory and the thinking process. Chemotherapy-induced cognitive impairment typically involves one or more of the following symptoms, difficulty in concentrating and thinking and multitasking, decreased memory, shortened attention span and/or feelings of disorganization. Chemotherapy-induced cognitive impairment may result from a wide variety of chemotherapeutics.

The term "behavioral and psychological symptoms of dementia" refer to apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders due to dementia. It also refers to any physical or verbal behavior of dementia patients which has the effect of hurting or repelling others, and includes aggressive behaviors such as beating, kicking, biting and screaming. The behavioral and psychological symptoms of dementia include the behavioral and psychological symptoms of Alzheimer's disease (AD), Parkinson's disease (PD), Lewy body dementia (LBD), cognitive deficits in vascular dementia and frontotemporal dementia (FTD). Preferably, the behavioral and psychological symptoms of dementia is selected from apathy/indifference in AD, aggression in AD, agitation in AD, depression in AD, anxiety in AD, irritability/lability in AD, dysphoria in AD, aberrant motor behavior in AD, delusions in AD, hallucinations in AD, elation/euphoria in AD, psychosis in AD, disinhibition in AD, sleep and night time behavior disorders or appetite and eating disorders in AD, apathy/indifference in PD, aggression in PD, agitation in PD, depression in PD, anxiety in PD, irritability/lability in PD, dysphoria in PD, aberrant motor behavior in PD, delusions in PD, hallucinations in PD, elation/euphoria in PD, psychosis in PD, disinhibition in PD, sleep and night time behavior disorders or appetite and eating disorders in PD.

The phrase, "therapeutically effective amount" is defined as an amount of a compound of the present invention that (i) treats the particular disease, condition or disorder, (ii) eliminates one or more symptoms of the particular disease, condition or disorder and (iii) delays the onset of one or more symptoms of the particular disease, condition or disorder described herein.

The term, "pharmaceutically acceptable salt" as used herein refers to salts of the active compound and are prepared by reaction with the appropriate organic or inorganic acid or acid derivative, depending on the particular substituents found on the compounds described herein. The pharmaceutically acceptable salt includes but not limited to, mesylate, hydrochloride, oxalate, fumarate, succinate, benzene sulfonate, tartrate and the like. Preferably, the pharmaceutically acceptable salt is oxalate and fumarate salts. More preferably, the pharmaceutically acceptable salt is oxalate salt.

The term, "patient" as used herein refers to an animal. Preferably the term "patient" refers to mammal. The term mammal includes animals such as mice, rats, dogs, rabbits, pigs, monkeys, horses, pigeons, *Xenopus laevis*, zebrafish, guinea pigs and humans. More preferably the patient is human.

The Compound-1, as used herein is Isopropyl-3-{5-[1-(3-methoxypropyl) piperidin-4-yl]-[1,3,4]oxadiazol-2-yl}-1H-indazole oxalate which has the chemical structure;

The Compound-1 and its preparation have been described in U.S. Pat. No. 9,079,894 and U.S. Ser. No. 10/005,711 respectively.

The term, "treatment' or 'treating" as used herein refers to any treatment of a disease in a mammal, including: (a) slowing or arresting the development of clinical symptoms; and/or (b) causing the regression of clinical symptoms.

The term, "compound for use" as used herein embrace any one or more of the following: (1) use of a compound, (2) method of use of a compound, (3) use in the treatment of, (4) the use for the manufacture of pharmaceutical composition/medicament for treatment/treating or (5) method of treatment/treating/preventing/reducing/inhibiting comprising administering an effective amount of the active compound to a patient in need thereof.

EMBODIMENTS

The present invention encompasses all the examples described herein without limitation, however, preferred aspects and elements of the invention are discussed herein in the form of the following embodiments.

In one embodiment, the present invention relates to the method for treating the diseases or disorders mediated through 5-HT$_4$ receptor using a 5-HT$_4$ receptor agonist; wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treating dementia due to menopause, senile dementia, cognitive deficits associated with schizophrenia, depression, chemotherapy-induced cognitive impairment, and behavioral and psychological symptoms of dementia comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treating dementia due to menopause comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treating senile dementia comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treating cognitive deficits associated with schizophrenia comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treating depression comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to method of treating depression comprising administering to a patient in need thereof, a therapeutically effective amount of 5-HT$_4$ receptor agonist and a selective serotonin reuptake inhibitor; wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to method of treating depression comprising administering to a patient in need thereof, a therapeutically effective amount of Isopropyl-3-{5-[1-(3-methoxypropyl) piperidin-4-yl]-[1,3,4]oxadiazol-2-yl}-1H-indazole or a pharmaceutically acceptable salt thereof and a selective serotonin reuptake inhibitor; wherein the selective serotonin reuptake inhibitor is selected from paroxetine, citalopram, escitalopram, fluoxetine, sertraline, dapoxetine and vilazodone or a pharmaceutically acceptable salt thereof.

In another embodiment, the present invention relates to the method of treating chemotherapy-induced cognitive impairment comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treating behavioral and psychological symptoms of dementia comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treating behavioral and psychological symptoms of dementia selected from apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treatment of apathy/indifference in dementia, aggression in dementia, agitation in dementia, depression in dementia, anxiety in dementia, irritability/lability in dementia, dysphoria in dementia, aberrant motor behavior in dementia, delusions in dementia, hallucinations in dementia, elation/euphoria in dementia, psychosis in dementia, disinhibition in dementia, sleep and night time behavior disorders or appetite and eating disorders in dementia comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treating apathy/indifference in Alzheimer's disease, aggression in Alzheimer's disease, agitation in Alzheimer's disease, depression in Alzheimer's disease, anxiety in Alzheimer's disease, irritability/lability in Alzheimer's disease, dysphoria in Alzheimer's disease, aberrant motor behavior in Alzheimer's disease, delusions in Alzheimer's disease, hallucinations in Alzheimer's disease, elation/euphoria in Alzheimer's disease, psychosis in Alzheimer's disease, disinhibition in Alzheimer's disease, sleep and night time behavior disorders or appetite and eating disorders in Alzheimer's disease, apathy/indifference in Parkinson's disease, aggression in Parkinson's disease, agitation in Parkinson's disease, depression in Parkinson's disease, anxiety in Parkinson's disease, irritability/lability in Parkinson's disease, dysphoria in Parkinson's disease, aberrant motor behavior in Parkinson's disease, delusions in Parkinson's disease, hallucinations in Parkinson's disease, elation/euphoria in Parkinson's disease, psychosis in Parkinson's disease, disinhibition in Parkinson's disease, sleep and night time behavior disorders or appetite and eating disorders in Parkinson's disease comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treating dementia due to menopause, senile dementia, cognitive deficits associated with schizophrenia, depression, chemotherapy-induced cognitive impairment, and behavioral and psychological symptoms of dementia comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In another embodiment, the present invention relates to the method of treating dementia due to menopause comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In another embodiment, the present invention relates to the method of treating senile dementia comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In another embodiment, the present invention relates to the method of treating cognitive deficits associated with schizophrenia comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In another embodiment, the present invention relates to method of treating depression comprising administering to a patient in need thereof, a therapeutically effective amount of 5-HT$_4$ receptor agonist; wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In another embodiment, the present invention relates to method of treating depression comprising administering to a patient in need thereof, a therapeutically effective amount of a 5-HT$_4$ receptor agonist and a selective serotonin reuptake inhibitor; wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In another embodiment, the present invention relates to method of treating depression comprising administering to a patient in need thereof, a therapeutically effective amount of Isopropyl-3-{5-[1-(3-methoxypropyl) piperidin-4-yl]-[1,3,4]oxadiazol-2-yl}-1H-indazole oxalate and a selective serotonin reuptake inhibitor; wherein the selective serotonin reuptake inhibitor is selected from paroxetine, citalopram, escitalopram, fluoxetine, sertraline, dapoxetine and vilazodone or a pharmaceutical salt thereof.

In another embodiment, the present invention relates to the method of treating chemotherapy-induced cognitive impairment comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In another embodiment, the present invention relates to the method of treating behavioral and psychological symptoms of dementia comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In another embodiment, the present invention relates to the method of treating behavioral and psychological symptoms of dementia selected form apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In another embodiment, the present invention relates to the method of treatment of apathy/indifference in dementia, aggression in dementia, agitation in dementia, depression in dementia, anxiety in dementia, irritability/lability in dementia, dysphoria in dementia, aberrant motor behavior in dementia, delusions in dementia, hallucinations in dementia, elation/euphoria in dementia, psychosis in dementia, disinhibition in dementia, sleep and night time behavior disorders or appetite and eating disorders in dementia comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to the method of treating apathy/indifference in Alzheimer's disease, aggression in Alzheimer's disease, agitation in Alzheimer's disease, depression in Alzheimer's disease, anxiety in Alzheimer's disease, irritability/lability in Alzheimer's disease, dysphoria in Alzheimer's disease, aberrant motor behavior in Alzheimer's disease, delusions in Alzheimer's disease, hallucinations in Alzheimer's disease, elation/euphoria in Alzheimer's disease, psychosis in Alzheimer's disease, disinhibition in Alzheimer's disease, sleep and night time behavior disorders or appetite and eating disorders in Alzheimer's disease, apathy/indifference in Parkinson's disease, aggression in Parkinson's disease, agitation in Parkinson's disease, depression in Parkinson's disease, anxiety in Parkinson's disease, irritability/lability in Parkinson's disease, dysphoria in Parkinson's disease, aberrant motor behavior in Parkinson's disease, delusions in Parkinson's disease, hallucinations in Parkinson's disease, elation/euphoria in Parkinson's disease, psychosis in Parkinson's disease, disinhibition in Parkinson's disease, sleep and night time behavior disorders or appetite and eating disorders in Parkinson's disease comprising administering to a patient in need thereof, a therapeutically effective amount of a 5-HT$_4$ receptor agonist, wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In yet another embodiment, the present invention relates to use of a 5-HT$_4$ receptor agonist in the treatment of diseases or disorders mediated through 5-HT$_4$ receptor, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In yet another embodiment, the present invention relates to use of a 5-HT$_4$ receptor agonist in the treatment of dementia due to menopause, senile dementia, cognitive deficits associated with schizophrenia, depression, chemotherapy-induced cognitive impairment, and behavioral and psychological symptoms of dementia, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the treatment of dementia due to menopause, senile dementia, cognitive deficits associated with schizophrenia, depression, chemotherapy-induced cognitive impairment, and behavioral and psychological symptoms of dementia.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the treatment of dementia due to menopause.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the treatment of senile dementia.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the treatment of cognitive deficits associated with schizophrenia.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the treatment of depression.

In another embodiment, the present invention relates to use of a 5-HT$_4$ receptor agonist in combination with a selective serotonin reuptake inhibitor, for treatment of depression; wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in combination with a selective serotonin reuptake inhibitor for the treatment of depression; wherein the selective serotonin reuptake inhibitor is selected from paroxetine, citalopram, escitalopram, fluoxetine, sertraline, dapoxetine and vilazodone.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the treatment of chemotherapy-induced cognitive impairment.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the treatment of behavioral and psychological symptoms of dementia.

In another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the treatment of behavioral and psychological symptoms of dementia selected from apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders.

In another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the treatment of apathy/indifference in dementia, aggression in dementia, agitation in dementia, depression in dementia, anxiety in dementia, irritability/lability in dementia, dysphoria in dementia, aberrant motor behavior in dementia, delusions in dementia, hallucinations in dementia, elation/euphoria in dementia, psychosis in dementia, disinhibition in dementia, sleep and night time behavior disorders or appetite and eating disorders in dementia.

In another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the treatment of apathy/indifference in Alzheimer's disease, aggression in Alzheimer's disease, agitation in Alzheimer's disease, depression in Alzheimer's disease, anxiety in Alzheimer's disease, irritability/lability in Alzheimer's disease, dysphoria in Alzheimer's disease, aberrant motor behavior in Alzheimer's disease, delusions in Alzheimer's disease, hallucinations in Alzheimer's disease, elation/euphoria in Alzheimer's disease, psychosis in Alzheimer's disease, disinhibition in Alzheimer's disease, sleep and night time behavior disorders or appetite and eating disorders in Alzheimer's disease, apathy/indifference in Parkinson's disease, aggression in Parkinson's disease, agitation in Parkinson's disease, depression in Parkinson's disease, anxiety in Parkinson's disease, irritability/lability in Parkinson's disease, dysphoria in Parkinson's disease, aberrant motor behavior in Parkinson's disease, delusions in Parkinson's disease, hallucinations in Parkinson's disease, elation/euphoria in Parkinson's disease, psychosis in Parkinson's disease, disinhibition in Parkinson's disease, sleep and night time behavior disorders or appetite and eating disorders in Parkinson's disease.

In yet another embodiment, the present invention relates to use of Isopropyl-3-{5-[1-(3-methoxypropyl) piperidin-4-yl]-[1,3,4]oxadiazol-2-yl}-1H-indazole oxalate in the treatment of dementia due to menopause, senile dementia, cognitive deficits associated with schizophrenia, depression, chemotherapy-induced cognitive impairment, and behavioral and psychological symptoms of dementia.

In yet another embodiment, the present invention relates to use of Isopropyl-3-{5-[1-(3-methoxypropyl) piperidin-4-yl]-[1,3,4]oxadiazol-2-yl}-1H-indazole oxalate in the treatment of dementia due to menopause.

In yet another embodiment, the present invention relates to use of Isopropyl-3-{5-[1-(3-methoxypropyl) piperidin-4-yl]-[1,3,4]oxadiazol-2-yl}-1H-indazole oxalate in the treatment of senile dementia.

In yet another embodiment, the present invention relates to use of Isopropyl-3-{5-[1-(3-methoxypropyl) piperidin-4-yl]-[1,3,4]oxadiazol-2-yl}-1H-indazole oxalate in the treatment of cognitive deficits associated with schizophrenia.

In yet another embodiment, the present invention relates to use of Isopropyl-3-{5-[1-(3-methoxypropyl) piperidin-4-yl]-[1,3,4]oxadiazol-2-yl}-1H-indazole oxalate for treating depression.

In another embodiment, the present invention relates to use of a 5-HT$_4$ receptor agonist in combination with a selective serotonin reuptake inhibitor, for treatment of depression; wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In yet another embodiment, the present invention relates to use of Isopropyl-3-{5-[1-(3-methoxypropyl) piperidin-4-yl]-[1,3,4]oxadiazol-2-yl}-1H-indazole oxalate and a selective serotonin reuptake inhibitor, for the treatment of depression; wherein the selective serotonin reuptake inhibitor is selected from paroxetine, citalopram, escitalopram, fluoxetine, sertraline, dapoxetine and vilazodone.

In yet another embodiment, the present invention relates to use of Isopropyl-3-{5-[1-(3-methoxypropyl) piperidin-4-yl]-[1,3,4]oxadiazol-2-yl}-1H-indazole oxalate in the treatment of chemotherapy-induced cognitive impairment.

In yet another embodiment, the present invention relates to use of Isopropyl-3-{5-[1-(3-methoxypropyl) piperidin-4-yl]-[1,3,4]oxadiazol-2-yl}-1H-indazole oxalate for treating behavioral and psychological symptoms of dementia.

In another embodiment, the present invention relates to use of Isopropyl-3-{5-[1-(3-methoxypropyl) piperidin-4-yl]-[1,3,4]oxadiazol-2-yl}-1H-indazole oxalate in the treatment of behavioral and psychological symptoms of dementia apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders.

In another embodiment, the present invention relates to use of Isopropyl-3-{5-[1-(3-methoxypropyl) piperidin-4-yl]-[1,3,4]oxadiazol-2-yl}-1H-indazole oxalate in the treatment of apathy/indifference in dementia, aggression in dementia, agitation in dementia, depression in dementia, anxiety in dementia, irritability/lability in dementia, dysphoria in dementia, aberrant motor behavior in dementia, delusions in dementia, hallucinations in dementia, elation/euphoria in dementia, psychosis in dementia, disinhibition in dementia, sleep and night time behavior disorders or appetite and eating disorders in dementia.

In another embodiment, the present invention relates to use of Isopropyl-3-{5-[1-(3-methoxypropyl) piperidin-4-yl]-[1,3,4]oxadiazol-2-yl}-1H-indazole oxalate in the treatment of apathy/indifference in Alzheimer's disease, aggression in Alzheimer's disease, agitation in Alzheimer's disease, depression in Alzheimer's disease, anxiety in Alzheimer's disease, irritability/lability in Alzheimer's disease, dysphoria in Alzheimer's disease, aberrant motor behavior in Alzheimer's disease, delusions in Alzheimer's disease, hallucinations in Alzheimer's disease, elation/euphoria in Alzheimer's disease, psychosis in Alzheimer's disease, disinhibition in Alzheimer's disease, sleep and night time behavior disorders or appetite and eating disorders in Alzheimer's disease, apathy/indifference in Parkinson's disease, aggression in Parkinson's disease, agitation in Parkinson's disease, depression in Parkinson's disease, anxiety in Parkinson's disease, irritability/lability in Parkinson's disease, dysphoria in Parkinson's disease, aberrant motor behavior in Parkinson's disease, delusions in Parkinson's disease, hallucinations in Parkinson's disease, elation/euphoria in Parkinson's disease, psychosis in Parkinson's disease, disinhibition in Parkinson's disease, sleep and night time behavior disorders or appetite and eating disorders in Parkinson's disease.

In yet another embodiment, the present invention relates to use of a 5-HT$_4$ receptor agonist in the manufacture of a medicament for the treatment of diseases or disorders mediated through 5-HT$_4$ receptor, wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In yet another embodiment, the present invention relates to use of a 5-HT$_4$ receptor agonist in the manufacture of a medicament for the treatment of dementia due to menopause, senile dementia, cognitive deficits associated with schizophrenia, depression, chemotherapy-induced cognitive impairment, and behavioral and psychological symptoms of dementia, wherein the 5-HT$_4$ agonist is a compound, Isopropyl-3-{5-[1-(3-methoxypropyl) piperidin-4-yl]-[1,3,4] oxadiazol-2-yl}-1H-indazole or a pharmaceutically acceptable salt thereof.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the manufacture of a medicament for the treatment of dementia due to menopause, senile dementia, cognitive deficits associated with schizophrenia, depression, chemotherapy-induced cognitive impairment, and behavioral and psychological symptoms of dementia.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the manufacture of a medicament for the treatment of dementia due to menopause.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the manufacture of a medicament for the treatment of senile dementia.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the manufacture of a medicament for the treatment of cognitive deficits associated with schizophrenia.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the manufacture of a medicament for the treatment of depression.

In another embodiment, the present invention relates to use of a combination comprising therapeutically effective amount of a 5-HT$_4$ receptor agonist and selective serotonin reuptake inhibitor in the manufacture of a medicament for treatment of depression; wherein the 5-HT$_4$ receptor agonist is Isopropyl-3-{5-[1-(3-methoxypropyl) piperidin-4-yl]-[1,3,4]oxadiazol-2-yl}-1H-indazole or a pharmaceutically acceptable salt thereof.

In another embodiment, the present invention relates to use of a combination comprising therapeutically effective amount of Isopropyl-3-{5-[1-(3-methoxypropyl) piperidin-4-yl]-[1,3,4]oxadiazol-2-yl}-1H-indazole oxalate and selective serotonin reuptake inhibitor in the manufacture of a medicament for treatment of depression; wherein the selective serotonin reuptake inhibitor is selected from paroxetine, citalopram, escitalopram, fluoxetine, sertraline, dapoxetine and vilazodone.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the manufacture of a medicament for treatment of chemotherapy-induced cognitive impairment.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the manufacture of a medicament for the treatment of behavioral and psychological symptoms of dementia.

In yet another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the manufacture of a medicament for treatment of behavioral and psychological symptoms of dementia selected from apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders.

In another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof, in the manufacture of a medicament for treatment of apathy/indifference in dementia, aggression in dementia, agitation in dementia, depression in dementia, anxiety in dementia, irritability/lability in dementia, dysphoria in dementia, aberrant motor behavior in dementia, delusions in dementia, hallucinations in dementia, elation/euphoria in dementia, psychosis in dementia, disinhibition in dementia, sleep and night time behavior disorders or appetite and eating disorders in dementia.

In another embodiment, the present invention relates to use of Isopropyl-3-{5-[1-(3-methoxypropyl) piperidin-4-yl]-[1,3,4]oxadiazol-2-yl}-1H-indazole or a pharmaceutically acceptable salt thereof for treatment of apathy/indifference in Alzheimer's disease, aggression in Alzheimer's disease, agitation in Alzheimer's disease, depression in Alzheimer's disease, anxiety in Alzheimer's disease, irritability/lability in Alzheimer's disease, dysphoria in Alzheimer's disease, aberrant motor behavior in Alzheimer's disease, delusions in Alzheimer's disease, hallucinations in Alzheimer's disease, elation/euphoria in Alzheimer's disease, psychosis in Alzheimer's disease, disinhibition in Alzheimer's disease, sleep and night time behavior disorders or appetite and eating disorders in Alzheimer's disease, apathy/indifference in Parkinson's disease, aggression in Parkinson's disease, agitation in Parkinson's disease, depression in Parkinson's disease, anxiety in Parkinson's disease, irritability/lability in Parkinson's disease, dysphoria in Parkinson's disease, aberrant motor behavior in Parkinson's disease, delusions in Parkinson's disease, hallucinations in Parkinson's disease, elation/euphoria in Parkinson's disease, psychosis in Parkinson's disease, disinhibition in Parkinson's disease, sleep and night time behavior disorders or appetite and eating disorders in Parkinson's disease.

In yet another embodiment, the present invention relates to use of a 5-HT$_4$ receptor agonist in the manufacture of a medicament for the treatment of dementia due to menopause, senile dementia, cognitive deficits associated with schizophrenia, depression, chemotherapy-induced cognitive impairment, and behavioral and psychological symptoms of dementia, wherein the 5-HT$_4$ agonist is a compound, Isopropyl-3-{5-[1-(3-methoxypropyl) piperidin-4-yl]-[1,3,4]oxadiazol-2-yl}-1H-indazole oxalate.

In yet another embodiment, the present invention relates to use of Isopropyl-3-{5-[1-(3-methoxypropyl) piperidin-4-yl]-[1,3,4]oxadiazol-2-yl}-1H-indazole oxalate in the manufacture of a medicament for the treatment of dementia due to menopause.

In yet another embodiment, the present invention relates to use of Isopropyl-3-{5-[1-(3-methoxypropyl) piperidin-4-yl]-[1,3,4]oxadiazol-2-yl}-1H-indazole oxalate in the manufacture of a medicament for the treatment of senile dementia.

In yet another embodiment, the present invention relates to use of Isopropyl-3-{5-[1-(3-methoxypropyl) piperidin-4-yl]-[1,3,4]oxadiazol-2-yl}-1H-indazole oxalate in the manufacture of a medicament for the treatment of cognitive deficits associated with schizophrenia.

In yet another embodiment, the present invention relates to use of Isopropyl-3-{5-[1-(3-methoxypropyl) piperidin-4-yl]-[1,3,4]oxadiazol-2-yl}-1H-indazole oxalate in the manufacture of a medicament for the treatment of depression.

In another embodiment, the present invention relates to use of a combination comprising therapeutically effective amount of a 5-HT$_4$ receptor agonist and a selective serotonin reuptake inhibitor in the manufacture of a medicament for treatment of depression; wherein the 5-HT$_4$ receptor agonist is Isopropyl-3-{5-[1-(3-methoxypropyl) piperidin-4-yl]-[1,3,4]oxadiazol-2-yl}-1H-indazole oxalate.

In another embodiment, the present invention relates to use of a combination comprising therapeutically effective amount of Isopropyl-3-{5-[1-(3-methoxypropyl) piperidin-4-yl]-[1,3,4]oxadiazol-2-yl}-1H-indazole oxalate and selective serotonin reuptake inhibitor in the manufacture of a medicament for treatment of depression; wherein the selective serotonin reuptake inhibitor is selected from paroxetine, citalopram, escitalopram, fluoxetine, sertraline, dapoxetine and vilazodone.

In yet another embodiment, the present invention relates to use of Isopropyl-3-{5-[1-(3-methoxypropyl) piperidin-4-yl]-[1,3,4]oxadiazol-2-yl}-1H-indazole oxalate in the manufacture of a medicament for the treatment of chemotherapy-induced cognitive impairment.

In yet another embodiment, the present invention relates to use of Isopropyl-3-{5-[1-(3-methoxypropyl) piperidin-4-yl]-[1,3,4]oxadiazol-2-yl}-1H-indazole oxalate in the manufacture of a medicament for the treatment of behavioral and psychological symptoms of dementia.

In yet another embodiment, the present invention relates to use of Isopropyl-3-{5-[1-(3-methoxypropyl) piperidin-4-yl]-[1,3,4]oxadiazol-2-yl}-1H-indazole oxalate in the manufacture of a medicament for the treatment of behavioral and psychological symptoms of dementia selected from apathy/indifference, agitation, aggression, depression, anxiety, irritability/lability, dysphoria, aberrant motor behavior, delusions, hallucinations, elation/euphoria, psychosis, disinhibition, sleep and night time behavior disorders or appetite and eating disorders.

In yet another embodiment, the present invention relates to use of Isopropyl-3-{5-[1-(3-methoxypropyl) piperidin-4-yl]-[1,3,4]oxadiazol-2-yl}-1H-indazole oxalate in the manufacture of a medicament for the treatment of apathy/indifference in dementia, aggression in dementia, agitation in dementia, depression in dementia, anxiety in dementia, irritability/lability in dementia, dysphoria in dementia, aberrant motor behavior in dementia, delusions in dementia, hallucinations in dementia, elation/euphoria in dementia, psychosis in dementia, disinhibition in dementia, sleep and night time behavior disorders or appetite and eating disorders in dementia.

In another embodiment, the present invention relates to use of Isopropyl-3-{5-[1-(3-methoxypropyl) piperidin-4-yl]-[1,3,4]oxadiazol-2-yl}-1H-indazole oxalate in the manufacture of a medicament for the treatment of apathy/indifference in Alzheimer's disease, aggression in Alzheimer's disease, agitation in Alzheimer's disease, depression in Alzheimer's disease, anxiety in Alzheimer's disease, irritability/lability in Alzheimer's disease, dysphoria in Alzheimer's disease, aberrant motor behavior in Alzheimer's disease, delusions in Alzheimer's disease, hallucinations in Alzheimer's disease, elation/euphoria in Alzheimer's disease, psychosis in Alzheimer's disease, disinhibition in Alzheimer's disease, sleep and night time behavior disorders or appetite and eating disorders in Alzheimer's disease, apathy/indifference in Parkinson's disease, aggression in Parkinson's disease, agitation in Parkinson's disease, depression in Parkinson's disease, anxiety in Parkinson's disease, irritability/lability in Parkinson's disease, dysphoria in Parkinson's disease, aberrant motor behavior in Parkinson's disease, delusions in Parkinson's disease, hallucinations in Parkinson's disease, elation/euphoria in Parkinson's disease, psychosis in Parkinson's disease, disinhibition in Parkinson's disease, sleep and night time behavior disorders or appetite and eating disorders in Parkinson's disease.

In another embodiment, the present invention relates to a pharmaceutical composition for use in treating dementia due to menopause, senile dementia, cognitive deficits associated with schizophrenia, depression, chemotherapy-induced cognitive impairment, and behavioral and psychological symptoms of dementia comprising a 5-HT$_4$ receptor agonist, Isopropyl-3-{5-[1-(3-methoxypropyl) piperidin-4-yl]-[1,3,4]oxadiazol-2-yl}-1H-indazole or a pharmaceutically acceptable salt thereof and pharmaceutically acceptable excipients thereof.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents and the like.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compound of the instant invention or pharmaceutically acceptable salt thereof. The amount of the active compound or its pharmaceutically acceptable salt in the pharmaceutical composition(s) can range from about 1 mg to about 2000 mg or from about 5 mg to about 1800 mg or from about 5 mg to about 1000 mg or from about 7 mg to about 350 mg or in any range falling within the broader range of 1 mg to 2000 mg.

EXAMPLES

The examples given below are provided by the way of illustration only and therefore should not be construed to limit the scope of the invention.

Abbreviations

5-HT$_4$: 5-Hydroxytryptamine 4 receptor
ANOVA: Analysis of variance
BCCL: Bilateral common carotid artery ligation
cAMP: Cyclic adenosine monophosphate
CD1: Cluster of differentiation 1
EC$_{50}$: Half maximal effective concentration
EDTA: Ethylenediamine tetra acetic acid
GPCR: G-Protein Coupled Receptor
HCl: Hydrochloric acid
h: Hour(s)
i.p.: Intraperitoneal
i.v.: Intravenous
i.m: Intramuscular
K$_i$: Inhibitory constant
mg: Milligram
MgCl$_2$: Magnesium chloride
min: Minute(s)
mM: Millimolar
nmol/L: Nanomoles per litre
nM: Nanomolar
p.o.: Per oral
s.c.: Subcutaneous
S.E.M.: Standard error of the mean
µM: Micromolar

Example 1

Determination of EC$_{50}$ Values at 5-HT$_4$ Receptor:

A stable CHO cell line expressing recombinant human 5-HT$_4$ receptor and pCRE-Luc reporter system was used for cell-based assay. The assay offers a non-radioactive based approach to determine binding of a compound to GPCRs. In this specific assay, the level of intracellular cAMP which is modulated by activation or inhibition of the receptor is measured. The recombinant cells harbor luciferase reporter gene under the control of cAMP response element. The above cells were grown in 96 well clear bottom white plates in Hams F12 medium containing 10% fetal bovine serum (FBS). Prior to the addition of compounds or standard agonist, cells were serum starved overnight. The reference endogenous agonist serotonin and test compounds in Opti-MEM medium at 11 different test concentrations starting from 10 µM until 0.1 nM in three-fold serial dilutions were incubated with the cells separately in individual wells for 4 hours at 37° C. in 5% CO$_2$. Medium was removed and cells were washed with phosphate buffered saline. The luciferase activity was measured in individual wells using luciferin substrate in Victor Light Luminometer Perkin Elmer. The maximum response produced by each drug was normalized to the 5-HT induced maximum response. Data was analyzed using Graphpad prism software to derive EC$_{50}$ values that correspond to the concentration of agonists required to obtain half-maximal stimulation of adenylyl cyclase.
Reference: *British Journal of Pharmacology.* 2000, 129, 771-781.
Results:

Compound-1 exhibits agonistic activity in cell based reporter gene assay an end point luminescence assay on human recombinant 5-HT$_4$ receptor. The EC$_{50}$ value of Compound-1 is 58.7±9.9 nM (E$_{max}$: 28.6±0.5%).

Example 2

Determination of K$_i$ Value at 5-HT$_4$ Receptor

Compound was tested at Caliper Life Sciences according to the following procedures.
Materials and Methods:
Receptor: Recombinant human 5-HT$_4$ receptor membrane protein
Radioligand: [3H]-GR113808 (83.9 Ci/mmol)
Final ligand concentration—[0.2 nM]
Non-Specific Ligand: 10 µM Serotonin (5-HT)
Reference compound: Serotonin
Positive control: Serotonin
Incubation conditions: Reactions were carried out in 50 mM Tris-HCl (pH 7.4) for 30 minutes at 25° C. The reaction was terminated by rapid vacuum filtration onto the glass fiber filters. Radioactivity trapped onto the filters was determined and compared to the control values in order to ascertain any interactions of the test compound(s) with the serotonin 5-HT4 binding site.
Reference: *British Journal of Pharmacology.* 1993, 109, 618-24.
Results:

Compound-1 selectively binds to 5-HT$_4$ receptor when tested by the in-vitro radio ligand binding technique on human recombinant 5-HT$_4$ receptor. The in-vitro K$_i$ value of Compound-1 is 23.9 nM.

Example 3

Figure 1:
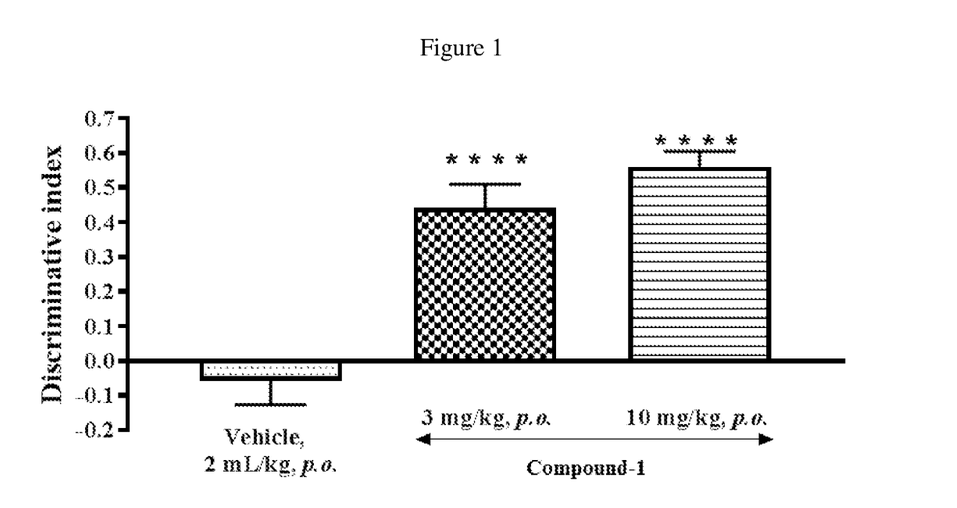
FIG. 1 depicts the effect of Compound-1 on cognition enhancing properties using object recognition task in ovariectomized rats.

Object Recognition Task (In Vivo Model for Dementia Due to Menopause):

Bilateral ovariectomy surgery was carried out in 7-8 weeks old female rats. Briefly, animals were anesthetized using Avertin (2,2,2-tri bromo ethanol) at 150 mg/kg, i.p. and were lay down on the surgery table. A midline incision was given on the dorsal region below the rib cage and 1 cm lateral to the either side of midline, a small incision was given on fascia to locate the adipose fat supporting the ovaries. By slowly pulling out the fat tissue, the ovary was identified and excised following the uterine horn ligation with silk sutures. Fascia was also covered with sutures and the similar procedure was repeated on the other side. Superficial skin layers were sutured and gentamicin (15 mg/kg, s.c.) was given as antibiotic and meloxicam (1 mg/kg, i.m.) as analgesic with povidone iodine applied on superficial skin layers at last. Episodic memory which is a memory of autobiographical events contextual in relation to time, place etc. was assessed ~12 months after the surgery using object recognition task. On experiment day 1, rats were transferred to experimental room for acclimatization. On experiment day 2, all groups of animals were habituated to their respective test arenas for a period of 30 min prior to trial-1. The compound-1 of instant invention was administered 60 min prior to trial-1. In trial-1, OVX aged female rats were presented with unfamiliar juvenile rat in their respective test arenas, i.e. home cage for a period of 5 minutes. Time spent by the adult rat socially investigating the juvenile was noted. After 60 min inter trial interval, adult rats were subjected to trial-2. In trial-2, aged OVX rats were presented with the familiar juvenile (presented during trial-1) along with a novel juvenile in their respective test arenas for a period of 5 min. Time spent by the adult rats socially investigating either familiar or novel juvenile in trial-2 was noted. Discriminative index (b−a3/b+a3) was calculated and compared among the groups.
Results:
Compound-1 reversed the object recognition memory deficits in ovariectomized female Wistar rats (FIG. 1).

Example 4

Figure 2:
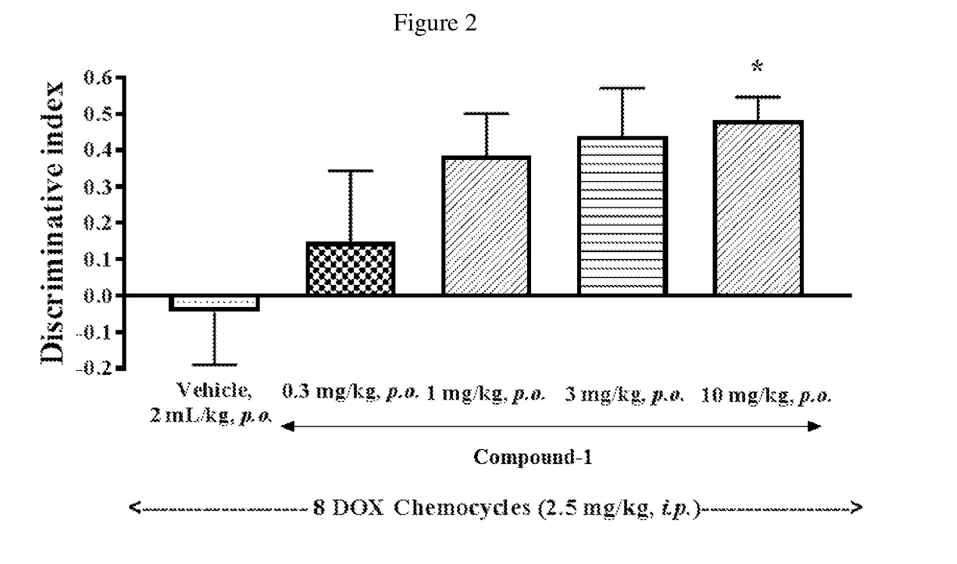
FIG. 2 depicts the effect of Compound-1 on memory deficits associated with DOX-induced cognitive impairment.

Object Recognition Task (In Vivo Model for Chemotherapy-Induced Cognitive Impairment):
The cognition-enhancing properties of Compound-1 in deficits associated with chemotherapy were estimated using an animal model of cognition i.e., object recognition task.
Male Wistar rats (230-280 g) were used as experimental animals. Four animals were housed in each cage. Rats were acclimatized for 7 days (Days 1-7) to the laboratory conditions. Chemotherapy-induced cognitive impairment was induced by injecting doxorubicin (DOX) at 2.5 mg/kg, i.p. once in every 5 days up to 8 cycles (days 8-49). Following 4 cycles, rats were also treated with compound-1 along with DOX, i.p. The object recognition task was carried out in a 50×50 cm circular open field made up of acrylic. On experimental day 50, 60 min following treatment, animals were habituated to the arenas for 45 min. On day 51, animals were treated with their respective formulations 60 min prior to the familiarization trial ($T_1$) during which rats was presented with two similar objects i.e., silver Milton flasks ($a_1$ and $a_2$) for 3 min. After an interval of 30 min, rats were subjected to choice trial ($T_2$), with one familiar (silver, $a_3$) and one novel (red, b) object for a period of 3 min. During the $T_1$ and $T_2$ trials, exploration time of each object (defined as sniffing, licking, chewing or having moving vibrissae whilst directing the nose towards the object at a distance of less than 1 cm) were recorded separately by hand held stop watch.
Reference: *Behavioural Brain Research*, 1988, 31, 47-59.
Results:
Compound-1 has shown significantly higher discriminative index indicating positive effects on cognition (FIG. 2).

Example 5

Figure 3:
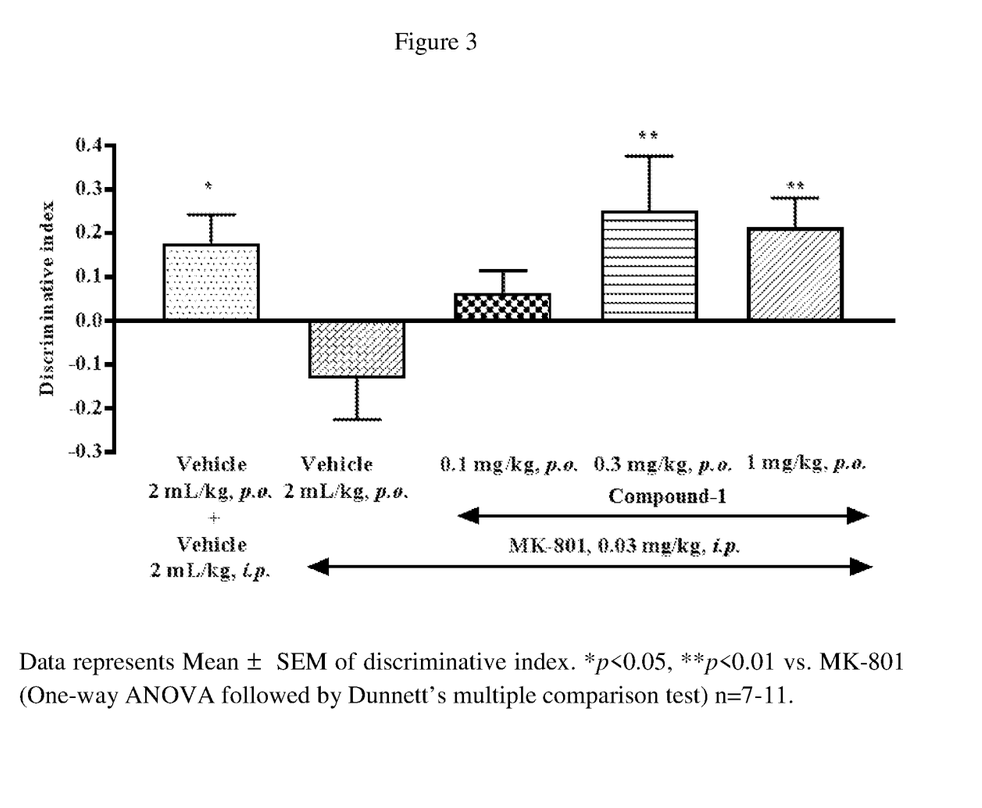
FIG. 3 depicts the effect of Compound-1 on memory deficits associated with MK-801 induced cognitive impairment.

Effect of Compound-1 on Memory Deficits Associated with MK-801 Induced Cognitive Impairment:
Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in a 50×50 cm circular arena made up of acrylic. Rats were habituated to individual arenas for up to 45 minutes in the absence of any objects on day 1.
On day 2, 60 minutes before the familiarization phase animals were administered vehicle or Compound-1 and 20 minutes before the familiarization phase the animals were administered vehicle or MK-801. During the familiarization phase, ($T_1$), the rats were placed individually in the arena for 3 minutes, in which two identical objects ($a_1$ and $a_2$) were positioned 10 cm from the wall. Ninety minutes after $T_1$, choice phase was performed. Rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch. Discriminative index was calculated as ratio of time spent exploring the novel object minus time spent exploring the familiar object divided by sum of time spent exploring the novel object and familiar object in choice trial (FIG. 3).
Reference: The object recognition test was performed as described by Ennaceur, A., Delacour, J., 1988, A new one-trial test for neurobiological studies of memory in rats—Behavioural data, Behav. Brain Res., 31, 47-59.
Result: Compound-1 reversed the MK-801 induced memory deficit at doses of 0.3 and 1 mg/kg, p.o. in NORT (FIG. 3).

Example 6

Effect of Compound-1 on Dominant Submissive Model (DSM) for Depression:
The testing apparatus was constructed from transparent plastic and consisted of two identical chambers (24×17×14 cm) connected by a tunnel (6×6×52 cm). A total of 220 male Wistar rats (110 pairs) of ~150-200 g weight were selected. The animals were randomized on the basis of body weight and matched for body weight, pair wise. The pairs were habituated to the testing apparatus and milk for a period of 5 min per day for 5 days (first week). The animals were housed such that these pairs met only during the trial time. Each pair was given equal access to milk containing 9% sucrose in a beaker (10 mL), which was placed in an opening on the floor at the midpoint of the tunnel. During the second week, time spent in drinking the milk by a pair of rats was recorded and scored for a period of 5 min. Once the 5 min period was over, the rat pair was returned to their respective home cages. Pairs of rats that met the following criteria were selected in the study.
1) The difference in the average drinking score of a pair was significant (two-tailed-t-test, $p<0.05$)
2) The dominant animal's score is greater by 25% than the submissive animal's score.

Figure 4:
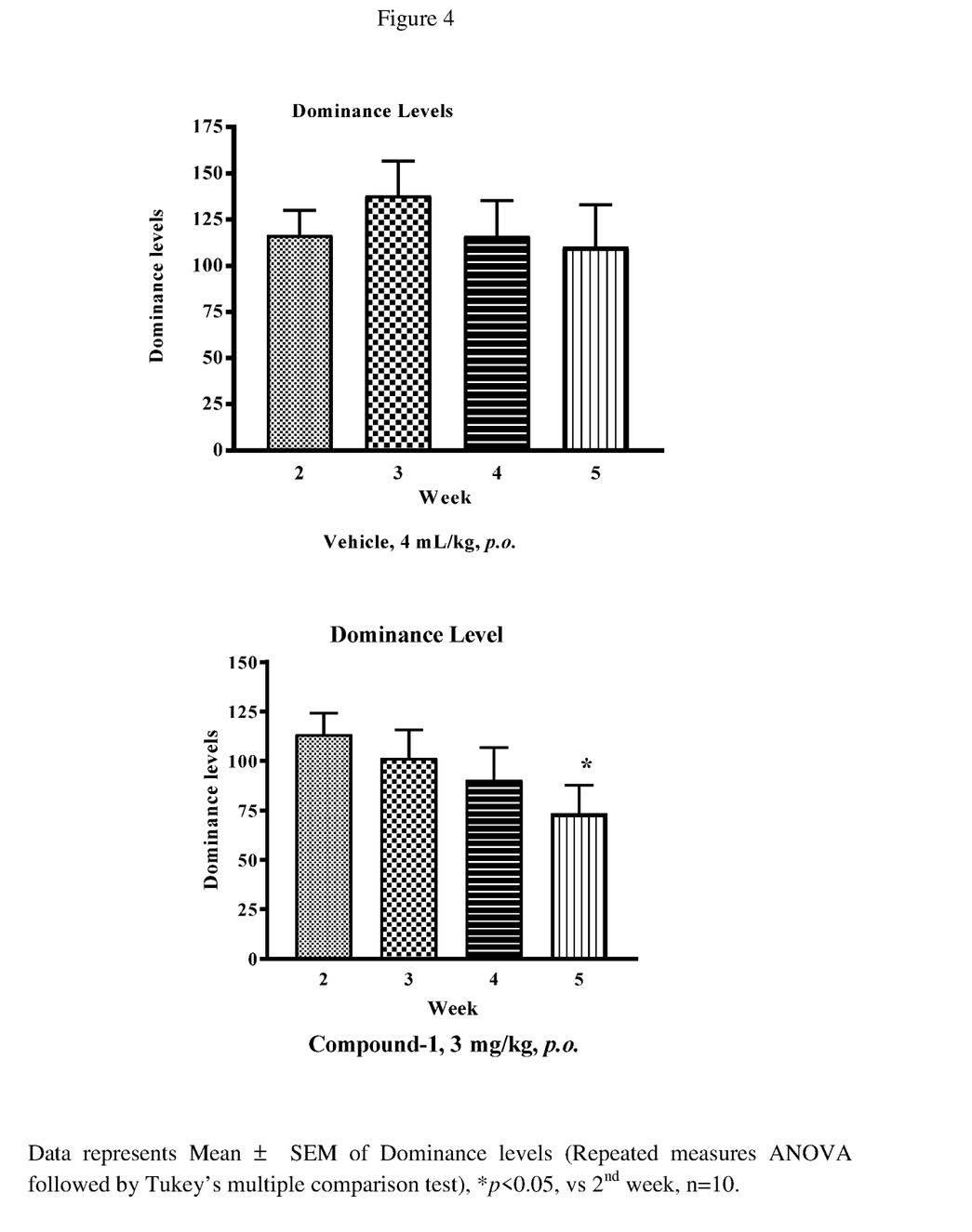
FIG. 4 depicts the effect of Compound-1 on Dominant Submissive model (DSM) for depression.

Pairs, which met the above criteria were selected and randomized based on the dominance levels. Both the dominant and submissive animals of the control group were treated with vehicle (sterile water, 4 mL/kg, p.o.). For the Compound-1 treatment groups, submissive animals were treated with Compound-1 (3, mg/kg, p.o.) and their dominant partners were treated with vehicle (sterile water, 4 mL/kg, p.o.). During the test period (three weeks), time spent in drinking the milk was recorded for each animal of a pair for a period of 5 min. Once the trial was over for all the animals in the group, they were given free access to food for 1 h. Treatments were administered 1 hour prior to trial on the days of testing and on the non-testing days treatments were administered between 10 AM and 4 PM. Animals were given free access to food from Friday afternoon to Sunday evening (weekends, non-testing days). Dominance level (the average of difference in daily drinking score between the dominant and submissive partners during the testing period) was analyzed using repeated measure one way ANOVA followed by Tukey's test against its dominance level during $2^{nd}$ week (FIG. 4).
Result: The dominance levels of Compound-1, 3 mg/kg, p.o. treated group decreased during the time course of treatment period and attained significance in $5^{th}$ ($p<0.05$) week. However, the dominant submissive relationship formed during the second week remained unchanged in the group treated with vehicle 10 mL/kg, p.o. during the entire course of the study. Compound-1 showed antidepressant activity (FIG. 4).

Example 7

In Vivo Brain Microdialysis (Effect of Compound-1 and Paroxetine Combination on Serotonin Modulation in Ventral Hippocampus):

Under isoflurane anesthesia, male Wistar rats (240-300 g body weight) were stereotaxically implanted with a microdialysis guide cannula in ventral hippocampus (AP: −5.2 mm, ML: +5.0 mm, DV: −3.8 mm). Co-ordinates were taken according to atlas for the rat brain (Paxinos and Watson, 2004) with reference points taken from bregma and vertical from the skull. The rats were allowed to recover individually for four-five days in a round bottom Plexiglas bowl with free access to feed and water.

One day prior to the microdialysis experiment, rats were connected to a dual quartz lined two-channel liquid swivel (Instech, UK) on a counter balance lever arm, which allowed unrestricted movements of the animal. Approximately sixteen hour before start of study, a pre-equilibrated microdialysis probe (4 mm dialysis membrane) was inserted into the ventral hippocampus through the guide cannula. On the day of the study, probes were perfused with artificial cerebrospinal fluid (a CSF; 147 mM NaCl, 3.0 mM KCl, 1.2 mM $CaCl_2$, and 1.2 mM $MgCl_2$, pH 6.2) at a flow rate of 1.5 µL/min. After stabilization period of 1 hour, four basal samples were collected at 30 min intervals prior to the administration of paroxetine (5 mg/kg, i.p.). Thirty minutes, after administration of paroxetine, Compound-1 (3 mg/kg, p.o.) was administered and samples were collected for additional 3.5 hours. Dialysates were snap-freezed and stored at −70° C. prior to analysis. After completion of a dialysis session, animals were subjected for the verification of probe placement and correct probe placement was taken as a criterion for selection of data from an animal.

Quantification of serotonin using LC-MS/MS Concentrations of serotonin in dialysates were quantified using LC-MS/MS by the analytical method described in Nirogi et al. [2013] after slight modifications. Samples were subjected to derivatization with dansyl chloride and following precursor-product ion pairs were monitored with m/z 853.1-170.1, m/z 869.2-170.1 and m/z 643.3-170.1 for the dansylated dopamine, norepinephrine and serotonin respectively. The analytes were quantified using triple quadrupole tandem mass spectrometer in positive ionisation mode using atmospheric pressure ionisation source. A gradient elution method was used to separate analytes from the interferences on an Agilent Poroshell 120 EC-C18 outer porous micro particulate column.

Figure 5:
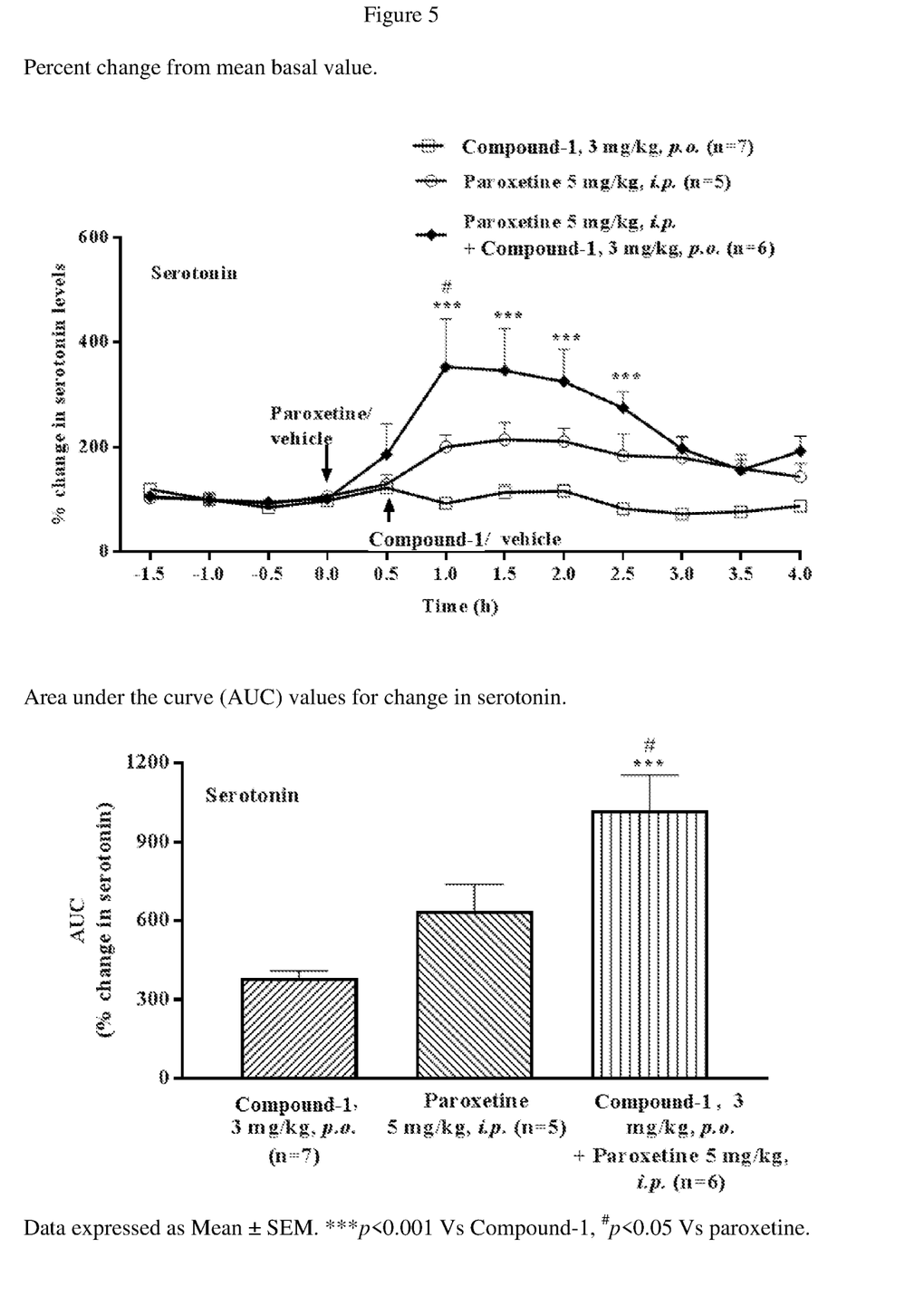
FIG. 5 depicts the effect of Compound-1 in combination of paroxetine on serotonin modulation in ventral hippocampus.

Statistical Analysis:

Absolute values (in nmol/L) of serotonin were converted into % change±SEM from mean basal value with 100% defined as the average of four pre-dose values. The statistical significance between the mean AUC values for percent change in neurotransmitter levels of treatment groups with vehicle was calculated using one way ANOVA followed by Dunnetts test. The percent change in serotonin levels after treatment was compared with paroxetine group using two-way analysis of variance (time and treatment), followed by Bonferroni multiple comparison test. Statistical analysis was carried out using Graph Pad Prism (Version 4) and significance was considered at a p value less than 0.05 (FIG. 5).

Incorrect probe placement was considered as criteria to reject the data from animal.

REFERENCES

1. Paxinos G. and Watson C. (2004) Rat brain in stereotaxic coordinates. Academic Press, New York
2. Nirogi R, et al. (2013) J Chromatogr B Analyt Technol Biomed Life Sci 913-914, 41-47.

Result: In combination with paroxetine, Compound-1 of present invention had produced synergistic effect on the extracellular levels of serotonin in the ventral hippocampus. Treatment with Compound-1 (3 mg/kg, p.o.) alone produced increase in hippocampal serotonin levels to the extent of 22% above pre-dose levels. Similarly, paroxetine (5 mg/kg, i.p.) alone produced increase in hippocampal serotonin levels to the mean maximum levels of 114% above pre-dose levels. Compound-1 in combination with paroxetine (5 mg/kg, i.p.) produced significantly higher increase in serotonin than it was observed with individual treatments or the sum of their effects on serotonin. Mean maximum increase in serotonin levels was observed to be 253% above pre-dose levels (FIG. 5).

Mean area under the curve values (AUC) calculated after combination treatment of Compound-1 and paroxetine were observed to be significantly higher compared to individual treatments alone.

Paroxetine augmenting effect upon Compound-1 administration suggests that a combined administration of an SSRI and a $5-HT_4$ receptor agonist (Compound-1) enhances 5-HT neurotransmission and offers a potential in the treatment of depression (FIG. 5).

Example 8

Resident Intruder Task:

Male CD1 mice of weight 20-35 g (Resident), 15-25 g (Intruder) and ovariectomized female mice (20-25 g) were used. Resident mice were habituated individually with ovariectomized female mice in each cage. β-estradiol at a dose of 0.2 mg/kg, s.c. was administered to female mice during habituation. Intruders were habituated socially for 1 week.

On day 1 and day 2, intruder was exposed to resident mice in resident's home cage for a period of 10 minutes and duration of attack was recorded. During this exposure period, female mice were removed from the cage. On day 4, animals were randomized based on their duration of attack and respective treatments were administered. Compound-1 (3, 10 and 30 mg/kg, p.o.) and vehicle were administered to resident mice 60 minutes prior to the trial. After post dose interval resident mice were exposed to same intruder for 10 min and duration of attack was recorded.

Figure 6:
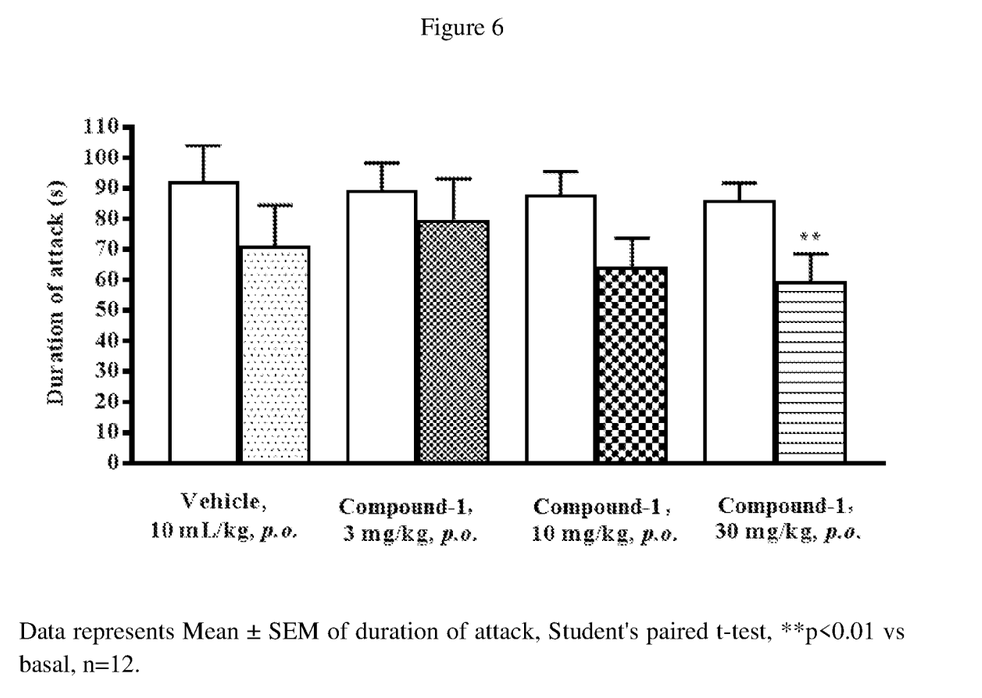
FIG. 6 depicts the effect of Compound-1 on aggression levels of CD1 mice.

Results:

Compound-1 decreased the aggression levels of CD1 mice at 30 mg/kg, p.o. (FIG. 6).

Example 9

Forced Swim Test in Mice:

Male Swiss albino mice of weight range, 30-45 g were used. Mice were dosed with vehicle or SUVN-D4010. Water was used as vehicle. After 30 minutes post treatment, animals of all the groups were individually placed inside the plexi glass cylinder (40 cm height×17 cm width) having 12 cm depth of water maintained at a temperature of 24±1° C. for 6 min. The duration of immobility and swimming of the mice in the last 4 minutes was recorded.

Figure 7:
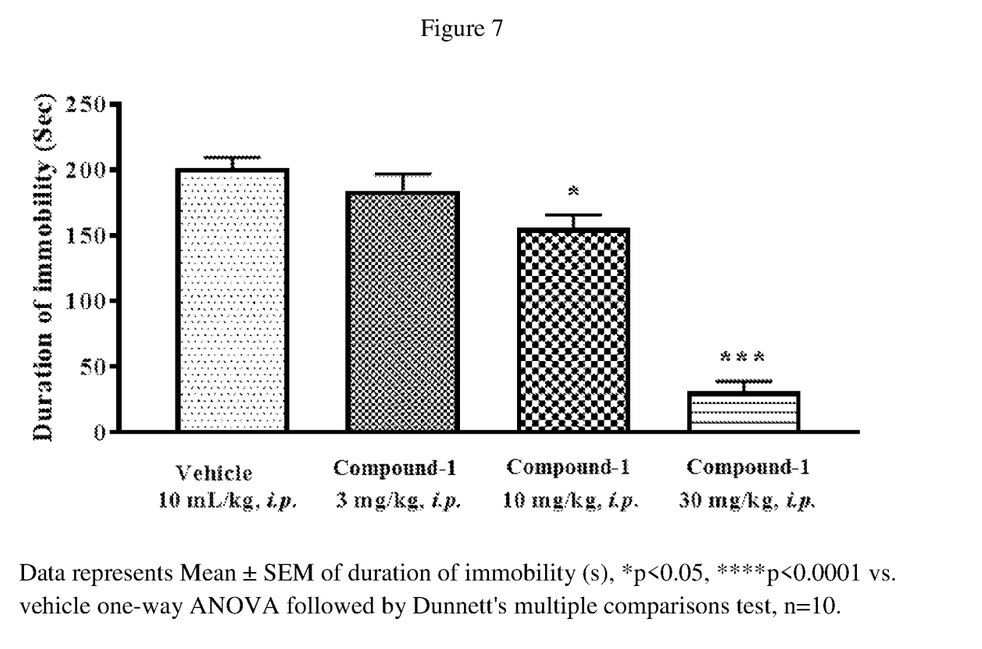
FIG. 7 depicts the effect of Compound-1 in Forced swim test in mice

Results: Compound-1 in significantly decreased the duration of immobility indicating antidepressant like effects (FIG. 7).

We claim:

1. A method of treating depression comprising the step of administering to a patient in need thereof, a therapeutically effective amount of a 5-$HT_4$ receptor agonist and a selective serotonin reuptake inhibitor, wherein the 5-$HT_4$ receptor agonist is a compound, Isopropyl-3-{5-[1-(3-methoxypropyl) piperidin-4-yl]-[1,3,4]oxadiazol-2-yl}-1H-indazole or a pharmaceutically acceptable salt thereof; and wherein the selective serotonin reuptake inhibitor is selected from the group consisting of paroxetine, citalopram, escitalopram, fluoxetine, sertraline, dapoxetine and vilazodone, or a pharmaceutically acceptable salt thereof.

2. The method as claimed in claim 1, wherein the pharmaceutically acceptable salt of Isopropyl-3-{5-[1-(3-methoxypropyl) piperidin-4-yl]-[1,3,4]oxadiazol-2-yl}-1H-indazole is selected from the group consisting of mesylate, hydrochloride, oxalate, succinate, fumarate and tartrate salt.

3. The method as claimed in claim 1, wherein the pharmaceutically acceptable salt of Isopropyl-3-{5-[1-(3-methoxypropyl) piperidin-4-yl]-[1,3,4]oxadiazol-2-yl}-1H-indazole is Isopropyl-3-{5-[1-(3-methoxypropyl) piperidin-4-yl]-[1,3,4]oxadiazol-2-yl}-1H-indazole oxalate.

4. The method of treating depression as claimed in claim 1, wherein the 5-$HT_4$ receptor agonist is Isopropyl-3-{5-[1-(3-methoxypropyl) piperidin-4-yl]-[1,3,4]oxadiazol-2-yl}-1H-indazole oxalate and the selective serotonin reuptake inhibitor is paroxetine or a pharmaceutically acceptable salt thereof.

* * * * *